United States Patent
Chen et al.

(10) Patent No.: US 10,172,932 B2
(45) Date of Patent: Jan. 8, 2019

(54) EBOLA VIRUS DISEASE VACCINE TAKING HUMAN REPLICATION DEFICIENT ADENOVIRUS AS VECTOR

(71) Applicant: Institute of Biotechnology, Academy of Military Medical Science, PLA, Beijing (CN)

(72) Inventors: Wei Chen, Beijing (CN); Shipo Wu, Beijing (CN); Lihua Hou, Beijing (CN); Xiaohong Song, Beijing (CN); Jinlong Zhang, Beijing (CN); Ling Fu, Beijing (CN)

(73) Assignee: Institute of Biotechnology, Academy of Military Medical Science, PLA, Beijing (CN)

( * ) Notice: Subject to any disclaimer, the term of this patent is extended or adjusted under 35 U.S.C. 154(b) by 0 days.

(21) Appl. No.: 15/760,093

(22) PCT Filed: Oct. 24, 2016

(86) PCT No.: PCT/CN2016/103016
§ 371 (c)(1),
(2) Date: Mar. 14, 2018

(87) PCT Pub. No.: WO2017/128783
PCT Pub. Date: Aug. 3, 2017

(65) Prior Publication Data
US 2018/0264100 A1 Sep. 20, 2018

(30) Foreign Application Priority Data
Jan. 31, 2016 (CN) .......................... 2016 1 0067289

(51) Int. Cl.
| | |
|---|---|
| *A61K 39/00* | (2006.01) |
| *C12N 7/00* | (2006.01) |
| *C12N 15/86* | (2006.01) |
| *C07K 14/005* | (2006.01) |
| *A61K 48/00* | (2006.01) |
| *A61K 39/12* | (2006.01) |
| *C12N 15/861* | (2006.01) |
| *A61P 31/14* | (2006.01) |

(52) U.S. Cl.
CPC .............. *A61K 39/12* (2013.01); *A61P 31/14* (2018.01); *C07K 14/005* (2013.01); *C12N 15/86* (2013.01); *C12N 15/861* (2013.01); *A61K 2039/5254* (2013.01); *A61K 2039/5256* (2013.01); *C12N 2710/10041* (2013.01); *C12N 2710/10062* (2013.01); *C12N 2710/10343* (2013.01); *C12N 2760/14122* (2013.01); *C12N 2760/14134* (2013.01)

(58) Field of Classification Search
CPC ........ C07K 14/005; C12N 15/86; C12N 7/00; C12N 2710/10343; A61K 39/12
See application file for complete search history.

(56) References Cited

FOREIGN PATENT DOCUMENTS

| | | |
|---|---|---|
| CN | 105483140 A | 4/2016 |
| WO | 2011130627 A2 | 10/2011 |

OTHER PUBLICATIONS

Richardson et al., "Enhanced Protection against Ebola Virus Mediated by an Improved Adenovirus-Based Vaccine," PLOS One (Apr. 23, 2009); 4(4):e5308 pp. 1-8.
Shipo, Wu, "Virulent pathogen vaccines based on recombinant adenoviral vector," CDFD Medicine and Hygiene Technology No. 11 (Nov. 15, 2013): pp. E059-62-7 to E059-62-18.

*Primary Examiner* — Barry A Chestnut
(74) *Attorney, Agent, or Firm* — Fox Rothschild LLP (57) ABSTRACT

Provided are an Ebola virus envelope glycoprotein (that is GP protein) codon optimized nucleotide sequence, a human replication deficient recombinant adenovirus capable of expressing the nucleotide sequence, and applications in preparing a vaccine for preventing Ebola virus diseases. The nucleotide sequence takes a replication deficient 5 type adenovirus that is lack of E1 and E3 in a combined mode as a vector. HEK293 cells that integrate adenovirus E1 genes serve as a packaging cell line, and carried protective antigenic genes are codon optimized Zaire type Ebola virus Makona strain envelope glycoprotein genes. After the envelope glycoprotein genes are optimized by codon, the expression level in transfection cells is obviously improved.

12 Claims, 6 Drawing Sheets
Specification includes a Sequence Listing.

SEQUENCE LISTING

<160> NUMBER OF SEQ ID NOS: 2

<210> SEQ ID NO 1
<211> LENGTH: 2037
<212> TYPE: DNA
<213> ORGANISM: Ebola virus

<400> SEQUENCE: 1
atcgaattcg ccgccaccat ggacgccatg aagcggggcc tctgctgtgt tctgctgctc        60
tgcggcgccg tgttcgtgag taactcgatc cctctgggcg tcatccataa ttccaccctg       120

```
caagtgtccg acgtggacaa gctcgtgtgc cgcgacaagc tgtccagtac caatcagctc      180
cgatccgtcg gtctcaacct ggagggcaac ggtgtcgcca ccgatgtgcc ctccgccacg      240
aagcggtggg gcttcagatc gggcgtgcct ccaaaggtcg taaactacga agccggcgaa      300
tgggccgaga actgttacaa tctggagatc aaaaagcctg atggaagtga gtgtctcccc      360
gcagcccctg acggaatccg aggttttcca aggtgcagat atgtgcacaa ggtctccggc      420
accgggccgt gcgcgggaga cttcgcattc acaaagagg gggcttttttt cctgtacgac      480
cggctggcgt ccacggtaat ttaccgggga acaaccttcg ccgagggcgt ggtcgccttc      540
ctcatcctgc tcaggctaa gaaggatttc ttctccagcc accccctgcg cgagcctgtg      600
aacgccacag aggacccctc tagtggctat tatagtacca caatccggta ccaggccacc      660
ggcttcggta ccaatgagac cgagtacctc tttgaggtgg ataacctcac ctacgtgcag      720
ctggagagtc gcttcacccc acagtttctg ctgcagctga tgagaccat ctatgcctcc       780
gggaagcgct ccaacaccac aggcaagctg atctggaagg tgaaccccga aattgataca      840
acaatcgggg agtgggcttt ctgggagacc aagaagaacc tcaccagaaa gatccgatcc      900
gaagagctgt ccttcacagc ggtctcgaat ggccccaaga acatatccgg ccagtcacct      960
gcccgcacca gttccgaccc cgaaaccaac actaccaacg aggaccacaa gatcatggca     1020
tccgagaaca gttcggcaat ggtacaggtg cacagtcagg gtcgaaaggc cgccgtgtca     1080
cacctcacca ccctcgccac tatctccact tcgcccagaa gtctgaccac caagccaggc     1140
cccgataact ccacgcataa cacaccagtg tacaagctcg acatctccga ggccacgcag     1200
gtcgggcagc accaccgccg ggccgataac gatagcacgg catcggacac ccctccagcc     1260
accaccgctg ccgggcctct gaaggcagaa ataccaaca catctaaatc cgcagactcc      1320
ctggacctgg ccaccactac ctctccccaa aactattctg aaacagcagg caacaataat     1380
acccaccacc aggacaccgg ggaggagtcc gcctcttccg gcaagctggg cctgattacc     1440
aacaccatcg ccgcgtggc cggctgattt acggcggac ggcggactcg acggaggtc       1500
atcgtgaatg cccaacccaa gtgtaacccg aacctccatt attggaccac gcaggacgaa     1560
ggcgctgcta tcggcctcgc ctggatcccc tactttggcc ccgccgccga gggtatctac     1620
actgagggcc tcatgcacaa tcaggatggc ctgatctgtg ggctcagaca gctggccaac     1680
gagaccaccc aggccctcca gttattctta agagccacca ccgagctgcg gacgttctct     1740
atcctcaaca gaaaagctat tgacttcctg ctccagcgat ggggcggtac ctgtcacatc     1800
ctggggcccg actgctgcat tgagcccccac gactggacaa aaaacataac cgataagatc     1860
gatcagatca tccacgattt cgtggacaag accctccccg accagggcga taacgacaac     1920
tggtggacag gctggcggca gtggataccc gccggtatcg gggtgaccgg tgtgatcatt     1980
gccgtcatcg cgctgttctg catctgcaag tttgtgtttt agagatctaa gcttgag       2037

<210> SEQ ID NO 2
<211> LENGTH: 2064
<212> TYPE: DNA
<213> ORGANISM: Ebola virus

<400> SEQUENCE: 2
atcgaattcg ccgccaccat gggtgttaca ggaatattgc agttacctcg tgatcgattc       60
aagaggacat cattctttct ttgggtaatt atccttttcc aaagaacatt ttccatcccg      120
cttggagtta tccacaatag tacattacag gttagtgatg tcgacaaact agtttgtcgt      180
gacaaactgt catccacaaa tcaattgaga tcagttggac tgaatctcga ggggaatgga      240
```

```
gtggcaactg acgtgccatc tgcgactaaa agatggggct tcaggtccgg tgtcccacca    300
aaggtggtca attatgaagc tggtgaatgg gctgaaaact gctacaatct tgaaatcaaa    360
aaacctgacg ggagtgagtg tctaccagca gcgccagacg ggattcgggg cttccccgg     420
tgccggtatg tgcacaaagt atcaggaacg ggaccatgtg ccggagactt tgccttccac    480
aaagagggtg ctttcttcct gtatgatcga cttgcttcca cagttatcta ccgaggaacg    540
actttcgctg aaggtgtcgt tgcatttctg atactgcccc aagctaagaa ggacttcttc    600
agctcacacc ccttgagaga gccggtcaat gcaacggagg acccgtcgag tggctattat    660
tctaccacaa ttagatatca ggctaccggt tttggaacta atgagacaga gtacttgttc    720
gaggttgaca atttgaccta cgtccaactt gaatcaagat tcacaccaca gtttctgctc    780
cagctgaatg agacaatata tgcaagtggg aagaggagca acaccacggg aaaactaatt    840
tggaaggtca accccgaaat tgatacaaca atcggggagt gggccttctg ggaaactaaa    900
aaaaacctca ctagaaaaat tcgcagtgaa gagttgtctt tcacagctgt atcaaacgga    960
cccaaaaaca tcagtggtca gagtccggcg cgaacttctt ccgacccaga gaccaacaca   1020
acaaatgaag accacaaaat catggcttca gaaaattcct ctgcaatggt tcaagtgcac   1080
agtcaaggaa ggaaagctgc agtgtcgcat ctgacaaccc ttgccacaat ctccacgagt   1140
ccccaatccc tcacaaccaa accaggtccg gacaacagca cccataatac acccgtgtat   1200
aaacttgaca tctctgaggc aactcaagtt ggacaacatc accgtagagc agacaacgac   1260
agcacagcct ccgacactcc ccccgccacg accgcagccg gacccttaaa agcagagaac   1320
accaacacga gtaagagcgc tgactccctg gacctcgcca ccacgacaag cccccaaaac   1380
tacagcgaga ctgctggcaa caacaacact catcaccaag ataccggaga agagagtgcc   1440
agcagcggga agctaggctt aattaccaat actattgctg gagtagcagg actgatcaca   1500
ggcgggagaa ggactcgaag agaagtaatt gtcaatgctc aacccaaatg caaccccaat   1560
ttacattact ggactactca ggatgaaggt gctgcaatcg gattggcctg gataccatat   1620
ttcgggccag cagccgaagg aatttacaca gaggggctaa tgcacaacca agatggttta   1680
atctgtgggt tgaggcagct ggccaacgaa acgactcaag ctctccaact gttcctgaga   1740
gccacaactg agctgcgaac cttttcaatc ctcaaccgta aggcaattga cttcctgctg   1800
cagcgatggg gtggcacatg ccacattttg ggaccggact gctgtatcga accacatgat   1860
tggaccaaga acataacaga caaaattgat cagattattc atgattttgt tgataaaacc   1920
cttccggacc aggggacaa tgacaattgg tggacaggat ggagacaatg gataccggca   1980
ggtattggag ttacaggtgt tataattgca gttatcgctt tattctgtat atgcaaattt   2040
gtcttttaga gatctaagct tgag                                          2064
```

EBOLA VIRUS DISEASE VACCINE TAKING HUMAN REPLICATION DEFICIENT ADENOVIRUS AS VECTOR

TECHNICAL FIELD

The present invention discloses an Ebola vaccine with a replication-defective human adenovirus as a vector, aims to preventing Ebola virus diseases, and belongs to the technical field of biotechnology.

BACKGROUND OF THE PRESENT INVENTION

Ebola virus, EBOV, belongs to filoviridae, and can cause hemorrhagic fever of human beings and non-human primates. Ebola virus was discovered in Southern Sudan and the Ebola River areas of Zaire in 1976 for the first time, and the virus was named as "Ebola" hence. A patient suffering from the virus has symptoms of fever, emesis, diarrhea, external and internal bleeding, brain, liver and kidney injury and the like, the mortality rate is as high as 50-90%. Diseases caused by Ebola virus infection were called as "Ebola hemorrhagic fever" before 2014, and after the Ebola epidemic outbreak in West Africa in 2014, the WHO and the US CDC changed the name of Ebola hemorrhagic fever to Ebola virus diseases, EVD.

At present, there are 5 subspecies of Ebola viruses: Zaire ebolavirus (EBOV), Sudan ebolavirus (SUDV), TaiForest ebolavirus (TAFV, which is also named as Cote d'Ivoire or Ivory Coast), Bundibugyoe ebolavirus (BDBV) and Reston ebolavirus (RESTV). There were reports that human beings were infected by the first four Ebola viruses and similar clinical symptoms were caused, and the diseases only happened in Africa at present. The Zaire ebolavirus (EBOV) has the strongest pathogenicity, and the Sudan ebolavirus (SUDV) has the second strongest pathogenicity.

Before the serious Ebola epidemic in West Africa in 2014, there were 24 Ebola epidemic events in the history, the death toll was about 1500 in all, the epidemic events mainly happened in Congo, Uganda, Sudan and the like in middle Africa, the outbreak generally occurred in sparsely populated areas, and the death toll of a single epidemic outbreak was never greater than 300. In 2014, the epidemic started from Guinea, and rapidly spread to countries around such as Liberia and Sierra Leone, a great number of EVD patients appeared in densely populated cities such as the capital Conakry of Guinea, the capital Freetown of Sierra Leone, the capital Monrovia of Liberia and the capital Lagos of Nigeria, and the virus had the characteristic of being propagated along traffic trunks, and was propagated to other areas out of the African continent for the first time, such as America, England, Spain and the like. The death toll has been approximate to 11 thousand in 2014-2015 Ebola epidemic There was no approved Ebola vaccine or treatment medicine in the world till March 2017. Many labs and pharmaceuticals companies are developing EBOV vaccines and treatment medicines. The vaccines include DNA vaccines, sub-unit vaccines, non-replication virus vector vaccines and replicable virus vector vaccines, and some DNA vaccines or vaccines based on live virus vectors already enter into clinical trials.

Ebola virus envelop Glycoprotein (GP) is the sole surface protein of an Ebola virus envelop, it has 2 reading frames, encoding a secretion small protein (sGP) and a whole-length transmembrane GP, respectively. GP is taken as a significant decisive factor of pathogenicity of the Ebola virus, and mediates virus enter the host cell by binding to a receptor, and is capable of damaging completeness of microvessels by binding to endothelial cells, and vascular leakage can be caused. At the same time, GP is also the main target protein inducing protective immune response. At present, all studies about the Ebola virus vaccines take GP (or GP and NP) as target antigen, and monoclonal antibodies (or antibody mixtures) which are proved to be effective in animal tests are all antibodies targeted to GP. Conventional inactivated vaccines and sub-unit vaccines are all ineffective on the Ebola virus, and vaccines which are being studied and are good in animal protection effect are ones which take GP as the target antigen and are based on virus vectors. How to obtain GP antigen as much as possible with a lowest immune dosage becomes an issue which needs to be solved urgently in development of Ebola vaccine.

An AdMax system consists of a shuttle plasmid with loxP site, a backbone plasmid and a HEK-293 cell strain, and after foreign gene sequences are constructed into the shuttle plasmid, the recombinant adenovirus can be generated through gene recombination with the backbone plasmid in HEK-293 cells.

The AdMax adenovirus system is a set of recombinant adenovirus construction system constructed by Frank Graham in 1999, and is developed as an adenovirus vector packaging system by the Micobix Company in Canada. The basic principle of the AdMax system for recombinant adenovirus packaging is that with Cre-loxP or FLP-frt recombinant enzymes, the shuttle plasmids and the backbone plasmids which are co-transfected into the HEK293 cells are subjected to site-specific recombination, generating the recombinant adenovirus. The recombinant virus obtained in such a manner is a replication defective with E1 loss, and the virus can only achieve foreign gene expression in cells without E1 area, and has no propagation ability. The AdMax system has the characteristic that recombinant virus generation is completed in a eukaryotic cell through the recombinant enzyme, is efficient and stable, and is one of the most convenient and rapidest adenovirus packaging systems at present.

Compared with most common AdEasy system at present, the AdMax system is relatively rapid in virus generation, and is capable of efficiently, simply, conveniently and rapidly acquiring the recombinant adenovirus, and moreover the yielding of the virus is greatly increased. By using the AdMax system, the whole process of plasmid construction to recombinant virus generation can be completed within only 2-4 weeks, the success rate is greater than 98% (95% of clone comprises target genes); since the recombinant virus generation is completed in the eukaryotic cell, the survival pressure to the adenovirus is maintained, and thus the completeness of a recombinant adenovirus genome can be maintained; however, the virus generation success rate of the AdEasy system is only 18-34% (the success rate of a new AdEasyXL system of the Stratagene company is about 94%), and in addition, because virus genome recombination is completed in a prokaryotic cell (BJ5183), theoretically, the adenovirus genome without the survival pressure can be relatively liable to mutate, and the virus inheritance background and the activity can be possibly affected.

Although the AdMax system has the advantages of being rapid in virus production, high in yielding and the like, as an effective live virus vector vaccine, in addition to advantages of the vector self, the system further needs to solve the significant issue how to more effectively express an inserted foreign target protein. If the foreign protein is too low in expression level, an effective immune effect is achieved by increasing the immune dosage, and the operation can definitely increase the adverse influence of the vector on inoculators. Therefore, optimizing the gene of the target protein so that the gene can be more effectively and correctly expressed, is an effective method for improving the immune effect of the vaccine.

On the basis of actual threat of the Ebola virus, the problem that in the prior art the vaccine prevention effect is not high in efficiency, and the technical difficulties of application of the AdMax system, the applicant intends to perform codon optimization on GP, so that the expression level of GP in the eukaryotic cell can be greatly increased, and the recombinant adenovirus vector Ebola vaccine which is relatively good in immunogenicity and capable of inducing antibodies of more high levels with a same dosage can be provided.

SUMMARY OF THE PRESENT INVENTION

On the basis of above purposes, the present invention firstly provides a nucleotide sequence of Ebola virus glycoprotein with codon optimization which is used in construction of a recombinant adenovirus vector Ebola vaccine. The nucleotide sequence is as shown in SEQ ID NO: 1. The nucleotide sequence adopts a replication-defective human type-5 adenovirus with deletion of E1 and E3 as a vector, and an HEK293 integrated with an adenovirus E1 gene as a packaging cell line, and the recombinant adenovirus vector Ebola vaccine is obtained through packaging.

The present invention further provides a vector comprising the nucleotide sequence.

In a preferred embodiment, the vector is pDC316.

The present invention further provides a human replication-defective recombinant adenovirus capable of expressing the nucleotide sequence.

In a preferred embodiment, the recombinant adenovirus vector is derived from an AdMax adenovirus system.

The present invention further provides a use of the recombinant adenovirus vector in preparing a vaccine for preventing the Ebola virus.

In a preferred embodiment of the use, the recombinant adenovirus is prepared as an injection.

Finally, the present invention provides a method for preparing the recombinant adenovirus capable of expressing the Ebola glycoprotein, and the method comprises the following steps:

(1) Constructing a shuttle plasmid comprising Ebola GP nucleotide coding sequences;

(2) Co-transfection of the vector of step (1) and backbone plasmids into a host cell;

(3) Culturing the host cell of step (2);

(4) Extracting the replication-defective recombinant human adenovirus which can express Ebola virus GP from the host cells of step (3).

Preferably, the vector of step (1) is pDC316.

Preferably, the backbone plasmid of step (2) is pBH-Glox_E1, 3Cre; the two plasmids both belong to an AdMax adenovirus system and are both used for packaging the recombinant adenovirus comprising the nucleotide sequence encoding Ebola GP in the host cell.

Preferably, the cell of step (3) is an HEK 293.

Preferably, the recombinant adenovirus is extracted and purified through a two-step column chromatography method with Source 30Q and Sepharose4FF in step (4).

The Ebola vaccine which is provided by the present invention can induce robust cellular and humoral immune response in immunized animals in a short time. The vaccine is simple in preparation, can be produced in a large scale within a short time, and can be applied to handle emergent Ebola epidemic events and biological terrorist attack. In addition, after codon optimization, the expression level of the GP in the transfected cells can be greatly increased, which result in greatly increased in humoral immune response induced by the recombinant adenovirus vector Ebola vaccine packaged this codon optimized GP. Increase of the immune response is significant to prevention of infection of the Ebola virus.

EXAMPLES

The present invention is further described with the combination of specific embodiments. The advantages and the characteristics of the present invention can be relatively clear with the description, but the embodiments are only exemplary and do not restrict the protection range of the present invention.

Embodiment 1 shows preparation of an Ebola vaccine which adopts a replication-defective recombinant human adenovirus 5 as a vector.

1. Codon Optimization and Synthesis of Ebola GP Gene.

Codon optimization on envelope glycoprotein gene of Zaire Ebola virus Makona strain (Genebank serial No.: KJ660346) which outbursts in Guinea in West Africa in 2014 by using Upgene software (Gao, W., Rzewski, A., Sun, H., Robbins, P. D., & Gambotto, A. (2004). UpGene: Application of a web-based DNA codon optimization algorithm. Biotechnol Prog, 20(2), 443-448.doi:10.1021/bp0300467), so as to enable the gene to be more suitable for expression in a eukaryotic cell, wherein the GP nucleotide sequence can be changed by 24.2% as a whole after codon optimization; meanwhile, changed a GP original signal peptide (1aa-32aa)

into a tissue plasminogen activator signal peptide tPA, and added a Kozak sequence in front of translation initiation codon, and performed gene synthesis; meanwhile, as control, synthesized original sequences of the envelope glycoprotein gene. See the codon optimization GP gene sequences (restriction enzyme cutting sites are EcoRI and HindIII) in SEQ ID NO:1, and see GP original gene sequence (restriction enzyme cutting sites are EcoRI and HindIII) in SEQ ID NO:2.

Figure 1A:
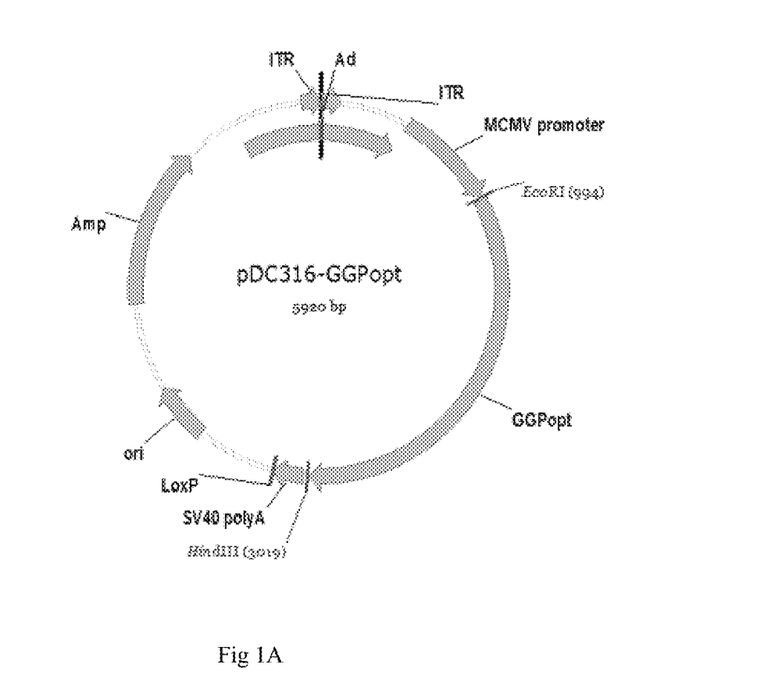
FIG. 1 shows the profile of the shuttle plasmid.
Figure 1B:
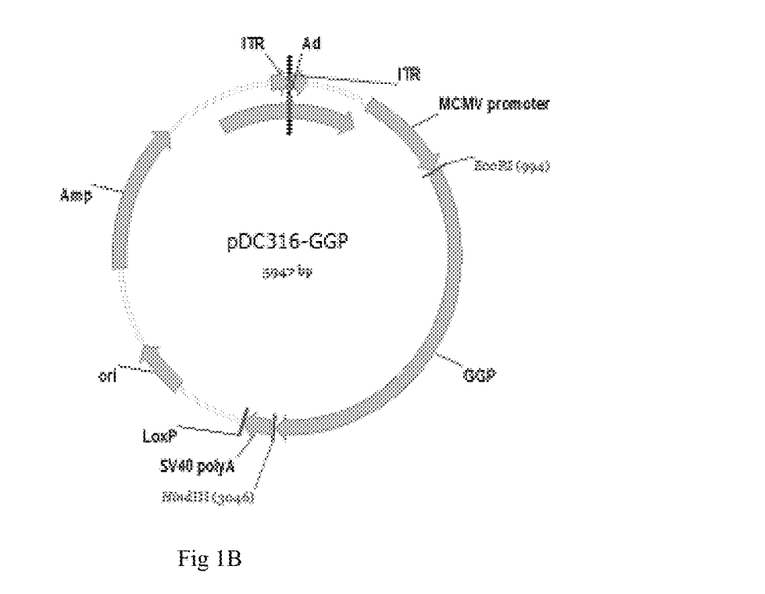

2. Vector Construction and Expression and Identification of GP In Vitro 2.1 Vector Construction Dual-enzyme digestion on the synthesized gene sequences was performed with EcoRI and HindI respectively. The target gene fragments were ligated with the shutter plasmids pDC316 of AdMax adenovirus system (Canada Microbix Biosystems Inc.), DH-5a competence bacteria was transformed with the recombinant plasmids, and plated on Ampr LB agar. Positive clones were identified by PCR and sequencing. pDC316-GGP referred to plasmids without codon optimization in the GP gene sequences as and the plasmids after GP gene codon optimization as pDC316-GGPopt, wherein plasmid profiles are as shown in FIG. 1, wherein A is a pDC316-GGPopt profile, and B is a pDC316-GGP profile.

2.2 Expression and Identification of GP In Vitro

Transfected the two constructed shuttle plasmids and the pDC316 vector into 293T cells by using a transfection reagent TurboFect Transfection Reagent, collected cells after 48 hours, and performed western blot detection, wherein a testing method comprises the following steps:

Transfection. The day before testing, 293T cells were inoculated into 6 well culture-plates in density of $8 \times 10^5$ cells/well, and cultured overnight in a cell incubator with 5% $CO_2$ at 37° C.; 1 h before transfection, medium was replaced with by a fresh MEM culture medium with 2% of fetal calf serum (FCS) in the volume of 2 ml per well; in transfection, 2 μg of corresponding plasmids was added into 200 μL of MEM medium without FCS for each transfection well, mixed with 3 μL of the transfection reagent, and left to stand for 15 min at room temperature; Then the mixed liquid of the plasmids and the transfection reagent were transferred into the 6-well plate, and the plate were placed in a cell incubator with 5% $CO_2$ at 37° C. The fresh MEM medium with 10% of FCS was replaced 5 h later and cells were collected 48 h later for western blot assay.

Sample preparation. After 48 h of transfection the medium was removed and the cells was washed once with PBS. The cells was resuspended with 120 μL of cell lysis liquid (50 mmol/L DTT, 1×protease inhibitor and 1×SDS-PAGE buffer of 250 U/mL nuclease) each well; The lysed cells were collected with a cell scraper and transferred into an EP tube of 1.5 mL, incubated on ice bath for 15 min, then heated for 5 min at 95° C., on ice bath for cooling again, centrifuged for 5 min with 12000 rpm at 4° C. The supernatant was collected for western blot assay.

Figure 2:
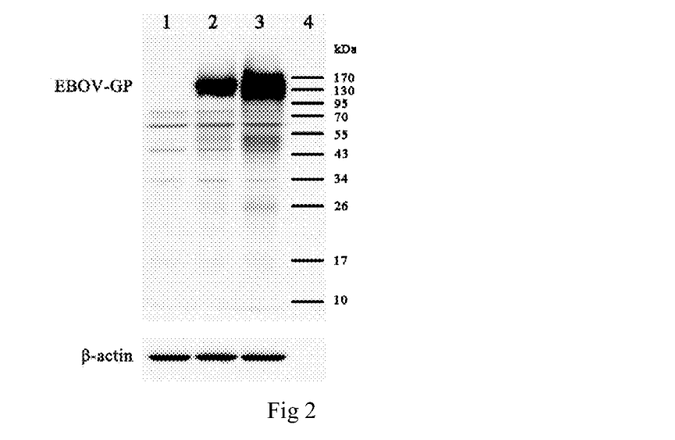
FIG. 2 shows the Western blot result of Ebola GP in transfected cells.

Western blot assay. The samples were loaded on 12% of SDS-PAGE gel and the electrophoresis conditions were 80V, 15 min and 180 V till bromophenol blue was just released from gel; Then the proteins on the SDS-PAGE gel were transferred into a nitric acid cellulose membrane through an electric transferring instrument, wherein the electric transferring conditions were 300 mA for 1 h; after electric transferring was completed, blocked the nitric acid cellulose membrane was blocked for 1 h with 5% of degreased milk powder, then a dilution degree of 1:500 of anti-Zaire Ebola GP rabbit serum was added to the blocking solution, and left to stand overnight at 4° C.; The nitric acid cellulose membrane was washed for 4 times with a wash buffer. Next the membrane was incubated in an HRP labeled goat anti-mouse IgG antibody which is diluted in 5% of the degreased milk powder in a ratio of 1:5000 for 1 h at room temperature. The membrane was washed for 4 times with the wash buffer, and the chemiluminescence reaction was performed by using Immobilon™ Western Chemiluminescent HRP Substrate (MILLIHOLE), and the images of different exposure times was acquired by a chemiluminescence imaging instrument, wherein the results were as shown in FIG. 2, that is, 1 refers to the cell sample transfected with a pDC316 empty vector; 2 refers to a pDC316-GGP transfected cell sample; 3 refers to a pDC316-GGPopt transfected cell sample; 4 refers to a standard protein marker; the result showed that GP can be well expressed in the transfected 293T cells; the expression level of the GP after codon optimization is somehow increased; in accordance with gray degree analysis, the expression level of the GP after codon optimization in the 293T cells is about 2 times of that without codon optimization.

3. Vaccine Packaging, Preparation and Identification 3.1 Vaccine Packaging

For recombinant adenovirus packaging, the shuttle plasmid pDC316-GGP and pDC316-GGPopt were co-transfected with the backbone plasmid pBHGlox_E1, 3Cre of the AdMax adenovirus system into HEK 293 cells, respectively. The process was as follows:

a) one day before transfection, the HEK293 cells were inoculated into the 6-well plates, incubated overnight in the cell incubator with 5% $CO_2$ at 37° C., wherein $5 \times 10^5$ cells were added into each well, and MEM+10% FBS was adopted as the culture medium;

b) The medium was replaced with a fresh MEM medium containing 10% of FBS on the day of transfection; when cells grew till being 80-90% of the area of a bottom surface. The backbone plasmids (pHBGlox_E1, 3Cre) and the shuttle plasmids were transfected with Lipofectamine™ 2000 lipidosome in accordance with its operation instructions; The steps were specifically as follows:

(1) 4 μg of the backbone plasmids and 1 μg of the shuttle plasmids were mixed for each transfection well;

(2) The plasmids were diluted with 300 μL of an MEM medium without serum, and left to stand for 5 min at room temperature;

(3) 10 μL of the lipidosome was diluted with 300 μL of an MEM medium without serum, and left to stand for 5 min at room temperature;

(4) The two plasmids were mixed, left to stand for 30 min at a light shielded place at room temperature, and then slightly transferred into the plate;

c) 1 day after transfection, the cells were passaged into a flask of 25 $cm^2$, with an MEM medium with 5% of FBS, observed every day. When the cells fully grew on the bottom of the flask, cells were passaged into a flask of 75 $cm^2$ and observed for the virus generation phenomenon every day, wherein the virus generation phenomenon is that the cells grow large and round, take the shape of grapes, and have conspicuous plaque; collecting the virus was collected after the obvious cytopathic effect appeared.

d) The flask with the virus was placed into a refrigerator of −70° C. and next a water bath of 37° C., for three times repeatedly, so as to release the virus from the cells; The virus liquid was centrifuged for 5 min at the speed of 3000 rpm, the supernatant with the virus was collected, wherein the supernatant was just a first generation of a virus seed (P1) which can be used as a virus seed for large-scale virus amplification;

The first generation of the virus seed of the packaged recombinant adenovirus vector Ebola vaccine were labelled as Ad5-GGP and Ad5-GGPopt respectively.

3.2 Identification of the First Generation of the Virus Seed 3.2.1 PCR Amplification on EBOV-GP Sequences The sequences of EBOV-GP were amplified with a universal primer of the pDC316 vector, wherein the primer sequences were as follows:

pDC316-F:
ACGTGGGTATAAGAGGCG pDC316-R:
CGATGCTAGACGATCCAG

The genome of Ad5-GGP and Ad5-GGPopt were extracted through DNA/RNA extract kit (DP315, Tiangen) for PCR identification with the following primers.

PCR amplification conditions were as follows:

| | |
|---|---|
| Test article genome DNA | 1 μL |
| Upstream primer | 0.4 μL |
| Downstream primer | 0.4 μL |
| dNTP | 1.6 μL |
| LA Taq DNA Polymerase | 0.2 μL |
| 10*LA Buffer | 2 μL |
| ddH$_2$O | 14.4 μL |

Reaction Procedures:

| | | |
|---|---|---|
| 94° C. | 5 min | |
| 94° C. | 30 s | |
| 56° C. | 30 s | 30 cycles |
| 72° C. | 40 s | |
| 72° C. | 10 mins | |

Figure 3:
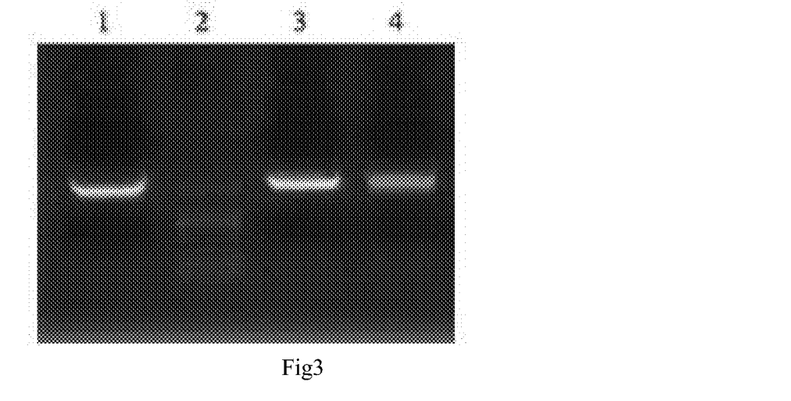
FIG. 3 shows the PCR identification result of the first-generation of recombinant adenovirus vector Ebola vaccine.

The PCR amplification result was as shown in FIG. 3, in the figure, 1 refers to positive control, 2 refers to standard DNA marker (Takara DL2000), 3 refers to an Ad5-GGPopt first generation virus seed DNA/RNA amplification product, and 4 refers to an Ad5-GGP first generation virus seed DNA/RNA amplification product; the FIG. 3 shows that target bands are all correct.

Figure 4:
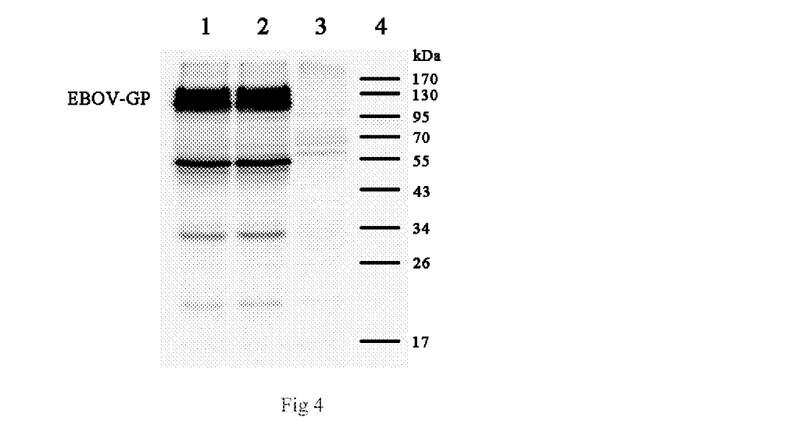
FIG. 4 shows the Western blot result of Ebola GP in recombinant adenovirus vector Ebola vaccine infected cells.

3.2.2 GP Expression and Identification of the Recombinant Adenovirus Vector Ebola Vaccine 293T cells were infected with the first generation of the virus seed of the Ad5-GGPopt and Ad5-GGP, the cells was collected 8 h later. Western blot was performed for GP expression, wherein the result showed that the target bands appeared in all cells which are infected by Ad5-GGPopt and Ad5-GGP, and the results were as shown in FIG. 4; in the figure, 1 refers to an Ad5-GGP infection cell sample, 2 refers to an Ad5-GGPpot infection cell sample, 3 refers to a blank cell sample, and 4 refers to a standard protein marker.

3.3 Amplification Culture and Purification of the Recombinant Adenovirus 3.3.1 Batch Culture of Recombinant Adenovirus Working Seeds HEK293 cells were infected once with the generation P1, and virus seed liquid was harvested as an original generation seed batch (labeled as a generation P2); The generation P2 was continuously passaged twice so as to construct a main seed batch (labeled as a generation P4), and from the generation P4, continuously passaged twice so as to construct a working seed batch (labeled as a generation P6).

3.3.2 Small-Scale Culture of Recombinant Adenovirus

HEK293 cells were cultured in suspension at the speed of 130 rpm under the conditions of 37° C. and 5% CO$_2$; The virus seeds were inoculated into the HEK293 cell at a MOI of 10 under the conditions of 37° C. and 5% of CO$_2$, wherein the final volume was 1 L. The samples were collected every 24 hours, and the activity and the density of the cells were monitored.

After the virus seeds were inoculated for 72 hours, and when the cell activity was degraded to be less than 40%, 10 mL of Tween-20 (final concentration was 1%) was added into each flask, and continuously shook for 1 h at the speed of 130 rpm; The harvest was centrifuged for 30 min at the speed of 6000 rpm. The supernatant was collected and stored at −70° C.; The precipitate was resuspended with isometric 20 mM Tris, 250 mM NaCl, 1 mM MgCl$_2$, pH 7.5. 1% of Tween-20 was added to the suspension, and it was shook for 1 h at 37° C. at the speed of 130 rpm; Then the suspension was centrifuged for 45 min at the speed of 6000 rpm, and the supernatant was collected and stored at −70° C.

3.3.3 Recombinant Adenovirus Purification

The collected recombinant adenovirus liquid in frozen preservation was melted and the adenovirus buffer was replaced with 20 mM Tris, 250 mM NaCl, 1 mM MgCl$_2$, pH 7.5 (liquid A) by using a 300 kDa ultra-filtration membrane packet. The Benzonase (30 U/mL) was added to the adenovirus solution and incubated at 37° C. for 4 h for degradation of host DNA.

Figure 5:
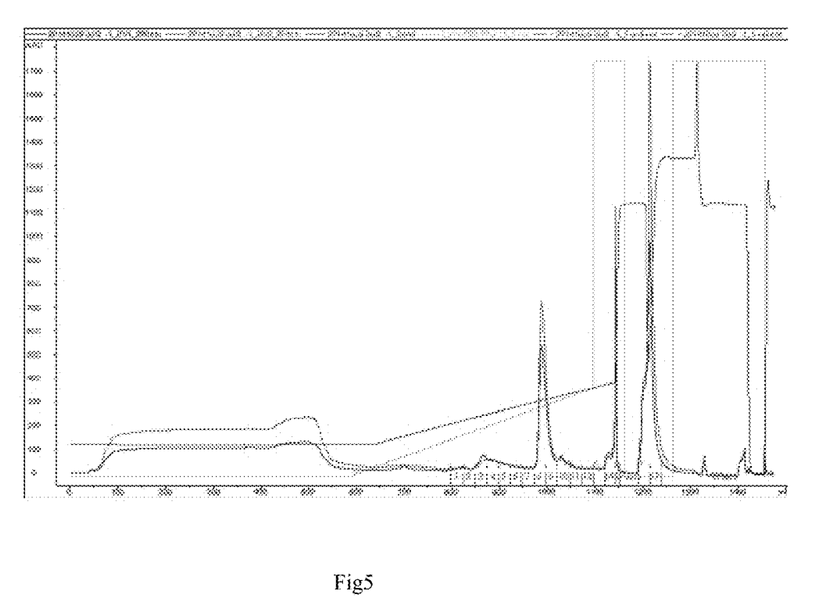
FIG. 5 shows the purification profile of Source 30Q chromatography.

The recombinant adenovirus was purified through Source 30Q and Sepharose 4 FF chromatography in two steps. In a first step, the main impurity proteins were removed and the elute with adenovirus were collected; In a second step, the impurity DNA molecules and a part of impurity proteins was removed and a flow through with adenovirus was collected; the specific procedures were as follows:

Source 30Q chromatography. Source 30Q column was balanced with the liquid A and the sample was loaded at 5 mL/min, wherein the Source 30Q chromatography process was as shown in FIG. 5; after the sample was loaded, the column was washed to a base line UV with the liquid A, The gradient elusion was performed from 0% B to 20% B in 50 min at 10 mL/min, and the elution peaks were collected. Finally, the column was eluted with 100% B, wherein a liquid B was 20 mM Tris+2 M, NaCl+2 mM MgCl$_2$ pH 7.5, and the peak elutions occurred in a buffer of which the NaCl concentration is about 530 mM.

Figure 6:
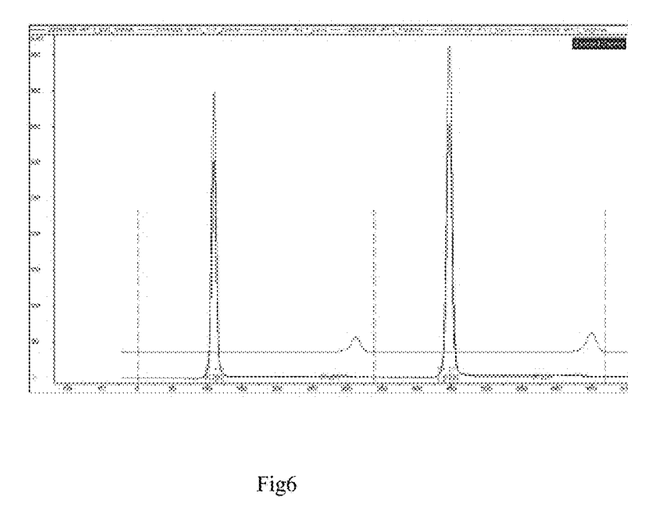
FIG. 6 shows the purification profile of Sepharose 4 FF chromatography.

Sepharose 4 FF chromatography. Sepharose 4 FF was chose for the next step, wherein the Sepharose 4 FF chromatography process was as shown in FIG. 6, the liquid A was adopted as a mobile phase, the velocity was 5 mL/min, the pressure limit was 0.3 MPa, and external flow through were collected; Finally the purified recombinant adenovirus was filtered for sterilization by using a disposable filter of 0.22 μm, and preserved in the refrigerator of −70° C.

Figure 7:
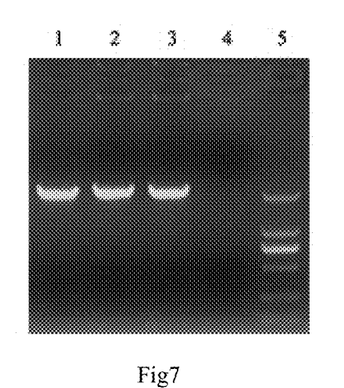
FIG. 7 shows the PCR identification result of the purified recombinant adenovirus vector Ebola vaccine.

3.4 Identification and Titering of the Recombinant Adenovirus Vector Ebola Vaccine Purified Sample 3.4.1 PCR Amplification of EBOV-GP Sequences and Sequencing The method was same as that of step 3.2.1, and showing the result in FIG. 7, wherein 1 refers to positive control, 2 refers to PCR product from an Ad5-GGPopt purified sample, 3 refers to PCR product from Ad5-GGP purified sample, 4 refers to negative control, and 5 refers to a standard DNA marker (Takara DL2000). The result showed that the target bands appeared in the purified sample. The sequences from the samples are all correct.

Figure 8:
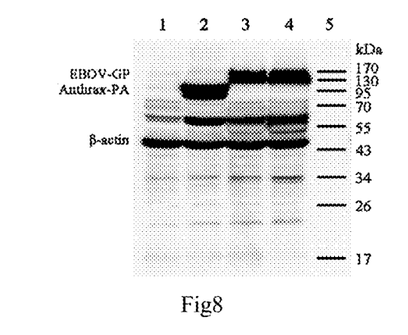
FIG. 8 shows the Western blot result of Ebola GP in cells infected with purified recombinant adenovirus vector Ebola vaccine.

3.4.2 Western Blot Assay 293T cells were infected with the purified recombinant adenovirus with MOI=10 and the cells were collected after 48 h for western blot on the GP, wherein the results were as shown in FIG. 8, in the figure, 1 refers to a blank cell sample, 2 refers to the control sample, a recombinant adenovirus which is capable of expressing *bacillus anthracis* protective antigen PA, 3 refers to an Ad5-GGP infected cell sample, 4 refers to an Ad5-GGPopt infected cell sample, and 5 refers to a standard protein marker. The figure showed that the target bands only occurred in the cells infected with the recombinant adenovirus expressing Ebola GP, and no target bands occurred in cells infected by the recombinant adenovirus in the control group, and blank cells.

3.4.3 Titer Testing

The recombinant adenovirus was titered by use of Clontech Adeno-X™ Rapid Titer Kit, the operation was implemented in accordance with the kit instructions, specifically as the following steps:

a) inoculated the HEK293 cells into a 24-well plate, wherein the cell density was $5 \times 10^5$ cells/mL; 0.5 mL of the cells was inoculated into each well; MEM+10% FBS was adopted as a culture medium;

b) diluted the virus for 10 times from $10^{-2}$ to $10^{-6}$ with the medium, and added 50 μL of the samples into the cells in the wells;

c) cultured for 48 h in the incubator with 5% $CO_2$ at 37° C.;

d) remove the culture medium of the cells, slightly dried the cells in air (not excessively dried), slightly added 0.5 mL of cold methanol into each well, left to stand for 10 min at −20° C. to immobilizing cells;

e) remove the methanol, slightly washed the cells for 3 times with PBS+1% BSA, added 0.25 mL of an anti-Hexon antibody diluent (dilution in a ratio of 1:1000) into each well, and incubated for 1 h at 37° C.;

f) remove anti-Hexon antibody, slightly washed the cells for 3 times with PBS+1% BSA, added 0.25 mL of HRP labeled Rat Anti-Mouse Antibody (dilution in a ratio of 1:1000) into each well, and incubated for 1 h at 37° C.;

g) before the 0.25 mL of HRP labeled Rat Anti-Mouse Antibody was removes, diluted a 10×DAB substrate as a 1×DAB working buffer with 1×Stable Peroxidase Buffer, and heated to room temperature;

h) remove the Rat Anti-Mouse Antibody diluent, and slightly washed the cells for 3 times with PBS+1% BSA, added 0.25 mL of a DAB working buffer into each well, and left to stand for 10 min at room temperature;

i) remove the DAB working buffer, and slightly washed the cells twice with PBS;

j) counted brown/black positive cells under a microscope, randomly calculated 3 views of each well, and calculated an average positive cell number;

k) calculated infection titer (ifu/mL), wherein the equation was as follows:

$$\text{Infection titer } (ifu/mL) = \frac{(\text{infected cells/field}) \times (\text{fields/well})}{\text{volume virus (mL)} \times (\text{dilution factor})}$$

The titer testing result showed the infection titer of a peak elution of Sepharose 4 FF chromatography elution was up to $1.0 \times 10^{10}$ ifu/mL.

3.4.4 Electron Microscope Morphology Observation

3.4.4.1 Negative Staining

Figure 9A:
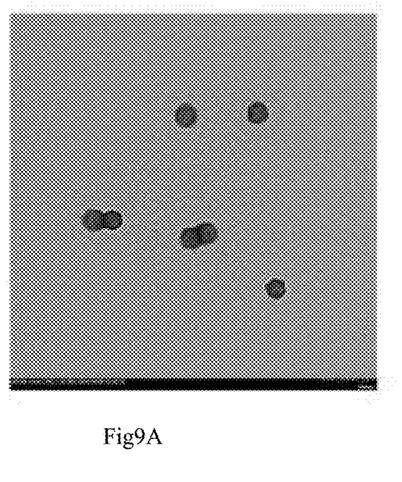
FIG. 9 shows the transmission electron microscope observation result of the negative stained purified recombinant adenovirus vector Ebola vaccine.
Figure 9B:
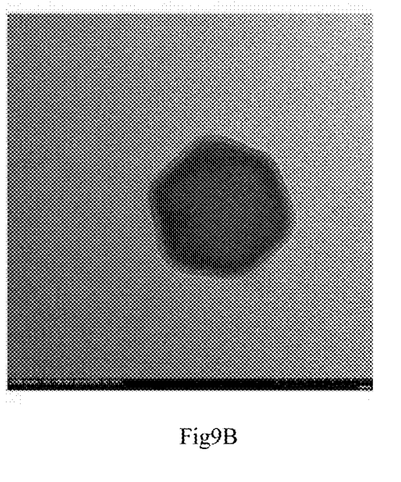

The purified recombinant adenovirus was loaded onto a carrier net, left to stand for 5-10 min, extra liquids on edges of the carrier net was removed with filter paper. The sodium phosphotungstate dyeing liquid was dropped when the carrier net is not completely dried. Extra liquids on edges of the carrier net was removed with the filter paper after dyeing for 3-5 min. The carrier net dried naturally, and was observed through a permeation electron microscope; the result was as shown in FIG. 9, in the figure, A refers to an observation result of amplification of 20,000 times, and B refers to an observation result of amplification of 150,000 times; the shape of the recombinant adenovirus vectored Ebola vaccine is identical to that of the adenovirus.

3.4.4.2 Performing Freezing Section

Figure 10A:
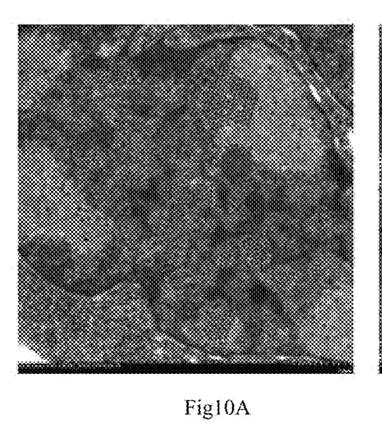
FIG. 10 shows the transmission electron microscope observation result of the frozen section of the recombinant adenovirus vector Ebola vaccine infected cells.
Figure 10B:
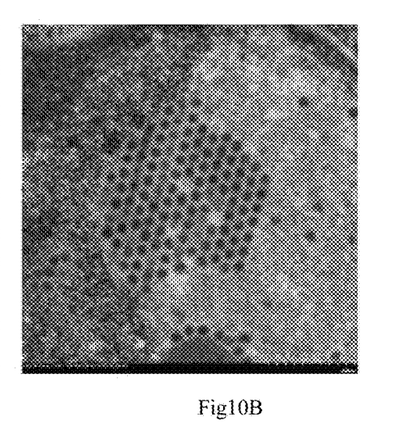

HEK293 cells were infected with the purified recombinant adenovirus (Ad5-GGPopt) at a MOI of 10. The cells were collected when the obvious cytopathic effect appeared. Freezing section treatment and permeation electron microscope observation were performed, and the results were shown in FIG. 10, in the figure, A refers to an observation result of amplification of 5,000 times, and B refers to an observation result of amplification of 15,000 times; the cells are full of adenovirus-like granules.

Embodiment 2 Immunological Evaluation on the Ebola Vaccine on a Mouse Model

1. Testing Materials

1.1 Testing Animals

SPF-grade female BALB/c mice (4-6 week old), purchased from the Testing Animal Center of the Academy of Military Medical Sciences, and the mice were bred in the Fengtai Animal Room of Beijing Institute of Biotechnology.

1.2 Reagents

Fluorescently-labeled antibodies PerCP/Cy5.5 Rat Anti-Mouse CD3e (clone 145-2c11), FITC Rat Anti-Mouse CD8a (clone 53-6.7), purchased from the Biolegend; PE Rat Anti-Mouse IFN-gamma (clone XMG1.2), Cytofix/Cytoperm™ Fixation and Permeabilization Solution, Perm/Wash™ Buffer, BD™ mouse IFN-gamma ELISPOT set, BD™ ELISPOT AEC substrate set and GolgiStop, purchased from the Becton, Dickinson and Company; self-made ACK erythrocyte lysate; RPMI1640 culture medium, purchased from HKB Science & Technology Co. Ltd; TMB, urea peroxide, PMA and ionomycin, purchased from Sigma-Aldrich; BSA, purchased from Merck; an HRP labeled anti-mouse IgG antibody, purchased from Santa Cruz; truncated Ebola-GP (46aa-364aa) was prepared in own lab; a control recombinant adenovirus vector Ad5-PAopt was constructed in own lab.

2. Mouse Immunization

The purified recombinant adenovirus vector Ebola vaccine (Ad5-GGPopt and Ad5-GGP) and the recombinant adenovirus vector control (Ad5-PAopt) were diluted to $2 \times 10^8$ ifu/mL with saline. The intramuscular injection were performed on the inner side of a left rear leg through an injector of 1 mL, 50 μL for each mouse, wherein the dose for each mouse was $1 \times 10^7$ ifu; the grouping of the mouse was as follows:

TABLE 1

Mouse for humoral immune response at different time point and cellular immune response detection at 22 weeks after immunization

| Vaccine | Dose | Number of mouse |
|---------|------|-----------------|
| Ad5-GGPopt | $10^7$ ifu | 10 |
| Ad5-GGP | $10^7$ ifu | 10 |
| Ad5-PAopt | $10^7$ ifu | 10 |

TABLE 2

Mouse for cellular immune response at 2 weeks after immunization

| Vaccine | Dose | Number of mouse |
|---------|------|-----------------|
| Ad5-GGPopt | $10^7$ ifu | 5 |
| Ad5-GGP | $10^7$ ifu | 5 |
| Ad5-PAopt | $10^7$ ifu | 5 |

3. Humoral Immune Response 3.1 Blood Collection and Serum Separation

Blood from tail vein of the mouse was collected at different time point and the blood was left to stand for more than 1 h at the room temperature. The serum was collected after the blood was centrifuged for 10 minu at the speed of 5000 rpm, freezed at −20° C.

3.2 Serum IgG by ELISA

The plates were coated with truncated Ebola-GP in the concentration of 4 μg/mL, and left to stand overnight at 4° C.; The liquid inside the wells was removed, and washed for 3 times with ELISA wash buffer (PBS+0.1% Tween-20); 120 μL of 2% BSA as blocking buffer was added into each well and blocked for 1 hour at 37° C. after wash for 3 times; 100 μL of a sample diluent (PBST+0.2% BSA) was added into each well for wash after the blocking buffer was removed. The serum samples were diluted as two-fold with a 8-dilution degree; two blank control wells without the serum were set on each plate; The diluted serum was incubated on the plates for 1 h at 37° C.; 100 μL of a secondary antibody (HRP-labeled goat anti-mouse IgG) was added into the plates after 3 times' wash, incubated for 50 min at 37° C. In the color reaction process, 50 μL of color solution A was first added into the plates, and 50 μL of color solution B was next added, mixed for 5 min, and the reaction was terminated with 50 μL/well of 2 mol/L sulfuric acid; Finally, the optical density values at 450 nm were read on a microplate reader, wherein wells with samples of which the $OD_{450}$ was 2.1 times greater than that of the blank wells were adopted as positive wells; the dilution fold of the positive wells with a largest dilution in each serum sample was recorded as the antibody titer of the sample.

Figure 11:
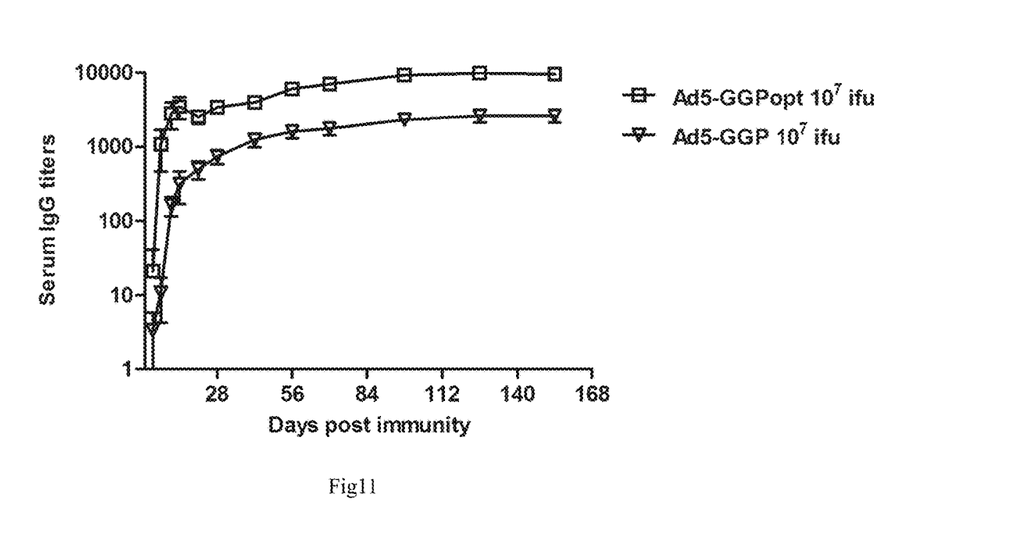
FIG. 11 shows the serum IgG level of the immunized mice.

The result was as shown in FIG. 11, mice immunized with Ad5-GGPopt can generate the anti-Ebola GP antibody within a relatively short time, and specific antibody can be detected 1 week after immunization; meanwhile, the antibody level can be relatively high, and the serum antibody titer was 4 times of that without codon optimization; in addition, the antibody titer can be maintained on a stable level within 22 weeks after immunization.

4. Cellular Immune Response 4.1 Splenocytes Separation

Mice were sacrificed by cervical dislocation, soaked in 70% alcohol for 3 min, then the spleens were taken out in a sterile manner, and the spleen was placed on a cell sieve of 200 meshes in a sterile flat dish; 10 mL of an RPM1640 complete culture medium was added, and the spleen was grounded into single cell with the piston of an injection, and next the cell sieve was washed with 20 mL of the RPM1640 complete culture medium so as to obtain more splenocytes; The splenocyte suspension was transferred into a centrifugal tube of 50 mL, and cells were centrifuged at 500×g for 5 min at 4° C.; The cells were re-suspended with 3 mL of ACK cell lysis solution and left to stand for 5 min at room temperature. Then 27 mL of the RPM1640 complete medium was added, and centrifuged at 500×g for 5 min at 4° C.; The precipitate was resuspended with 30 mL of the RPM1640 complete medium and the cells were filtered through the cell sieve of 200 meshes into a tube of 10 mL, and the cell density was counted.

4.2 the Specific Cytokines Response by Intracellular Cytokine Staining 4.2.1 In-Vitro Restimulation of Mouse Splenocytes The separated mouse spleen cells was diluted into $4 \times 10^6$ cells/mL and seeded into the 24-well plate at 0.5 mL per well; For a mouse, a stimulation well with specific CTL epitopes and a non-stimulation well with equal volume of DMSO were included, wherein the specific CTL epitopes were GF-9 and LV-9, and the concentration was 10 μg/mL; as positive control, splenocytes were stimulated with PMA and ionomycin, wherein the concentration of the PAM was 100 ng/mL; the concentration of ionomycin was 1 μg/mL; after the cells were cultured for 1 h in the incubator with 5% $CO_2$ at 37° C., a proper amount of GolgiStop (4 μL of GolgiStop acts on 6 mL of the cells) was added into each well to block cytokine secretion, after the cells were cultured for 6 h in all, the splenocytes were transferred into the 5 mL polystyrene round-bottom tube for intracellular cytokine staining.

4.2.2 Cell Surface Antigen Staining and Intracellular Cytokine Staining

After stimulation for 6 h, splenocytes were transferred into the 5 mL polystyrene round-bottom tube, centrifuged at 500×g for 5 minutes at 4° C., and collected; in accordance with the instruction, PerCP/Cy5.5-conjugated anti-CD3 (clone 145-2c11) and FITC conjugated anti-CD8 (clone 53-6.7) were diluted with PBS+2% FBS, then 50 μL of the diluted antibody mixture was transferred into each tube, slightly mixed uniformly, and left to stand for 30 minutes at 4° C.; 30 min later, 3 mL of PBS+2% FBS was added into each tube, centrifuged at 500×g for 5 min at 4° C., and the supernatant was removed; 200 μL of BD Cytofix/Cytoperm™ Fixation and Permeabilization Solution was added into each tube, left to stand for 20 min at 4° C.; 20 min later, 1 mL of 1×BD Perm/Wash™ Buffer was added into each tube, centrifuged at 600×g for 5 min at 4° C., and the supernatant was removed; The PE conjugated anti-IFN-gamma (clone XMG1.2) antibody was diluted 1×BD Perm/Wash™ Buffer with in accordance with the instruction, and 50 μL of the diluted antibody was added into each tube, slightly mixed uniformly, and left to stand for 30 min at 4° C.; Finally, the sample was washed once with 1 mL of 1× BD Perm/Wash™ Buffer and 3 mL of PBS respectively, and re-suspended with 200 μL of PBS after centrifugation. The secretion of IFN-gamma was assayed on a flow cytometer. In order to adjust the compensation of different dyes, the non-staining tube, PerCP/Cy5.5-conjugated anti-CD3 staining tube, FITC conjugated anti-CD8 staining tube and PE conjugated anti-IFN-gamma staining tube were included, wherein positive stimulated cells were used in the PE conjugated anti-IFN-gamma staining tube.

4.2.3 IFN-Gamma Assay by Flow Cytometry

Flow cytometry analysis was performed on Beckman Culter® CyAn™ ADP. Firstly, the appropriate voltage and the compensation among different dyes were adjusted. Lymphocytes were gated by FSC and SSC, and set as gate 1; from gate 1, CD3+ T cells were gated by FL3(PerCP/Cy5.5) and SSC, and set as gate 2; from gate 2, cells were diagrammed by FL1 (FITC) and FL2 (PE) and the percentage of CD8 and IFN-gamma dual positive cells to total T cells (CD3+ T cells) were analyzed; in other way, CD8+ T cells were gated for analyzing the percentage of IFN-gamma positive cells in CD8+ T cells; analyzed the detection results by Summit software which developed by Beckman Culter®.

Figure 12:
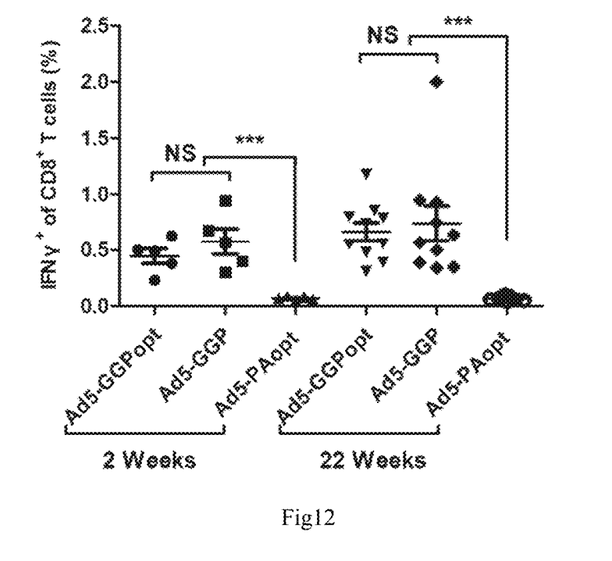
FIG. 12 shows the IFN gamma level in splenocytes of mice immunized with Ebola vaccine through intracellular cytokine staining.

As shown in FIG. 12, the result showed that at 2 weeks and 22 weeks after immunization, the IFN-gamma secretion level of CD8+ T cells from the mouse immunized with Ad5-GGPopt and Ad5-GGP were remarkably higher than that of the control, but the IFN-gamma secretion levels of Ad5-GGPopt and Ad5-GGP before and after codon optimization of the GP gene had no statistic differences.

4.3 Mouse IFN-Gamma ELISPOT Assay

ELISPOT assay of mouse IFN-gamma was performed with BD™ ELISPOT mouse IFN-gamma Set. According to the manual, the ELISPOT plates were coated with a 5 μg/mL of anti-mouse IFN-gamma antibody, and left to stand overnight at 4° C.; then the plates were blocked for 2 h with RPMI1640+10% FES medium at room temperature; Next 100 μL of the RPMI1640+10% FBS culture medium containing Ebola virus GP CTL epitope GF-9 and LV-9 was added into wells as Ebola CTL epitope stimulation well, RPMI complete medium with equal DMSO as non-stimulation well, wherein the concentration of GF-9 and LV-9 was 10 μg/mL; 100 μL of the mouse splenocytes was added into each well, wherein the cell concentration was $2 \times 10^6$ cells/mL; 40 ng/mL of PMA and 500 ng/mL of ionomycin were added into each positive control wells; beside, blank control wells without splenocytes were also included; the plates were incubated in the incubator with 5% $CO_2$ at 37° C. for 18-24 h; Next day, the cells were removed from the plate, and the plates were washed twice with distilled water and three times with wash buffer (PBS+0.1% Tween-20) sequentially, and left to stand for 2-3 min each wash; 100 μL of Biotinylated anti-mouse IFN-gamma diluted in PBS+10% FBS in a ratio of 1:250 was added into each well, and left to stand for 2 h at the room temperature; The liquid in the wells was remove 2 h later, and the plates were washed three times with wash buffer, left to stand for 2-3 min each time, and 100 μL of streptavidin-horseradish peroxidase diluted in PBS+10% FBS in a ratio of 1:100 was added into each well, and left to stand for 1 h; The plates were washed 4 times with wash buffer and three times with PBS sequentially; Color generation reaction developed with BD™ ELISPOT AEC substrate set; When the spots inside grew to the proper sizes (the reaction lasted 15-25 min at the room temperature generally), the plates were washed with a great deal of distilled water so as to terminate the reaction; The plates were dried in air, and the spots were counted with an ELISpot reader imaging analysis system.

Figure 13:
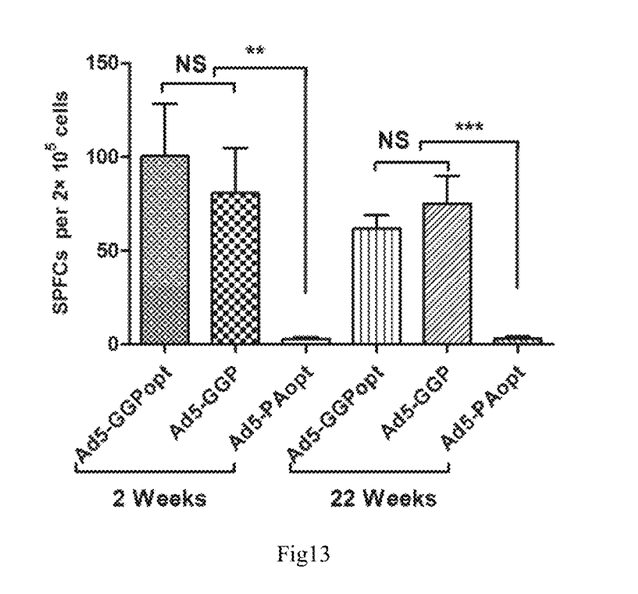
FIG. 13 shows the IFN gamma level in splenocytes of mice immunized with the vaccine through ELISPOT.

The result was as shown in FIG. 13, no matter at 2 weeks or 22 weeks after immunization, the number of IFN-gamma positive spots of the Ad5-GGPopt and Ad5-GGP immunized mouse was greatly higher than that of the control mouse; no matter at 2 weeks or 22 weeks after immunization, the number of IFN-gamma positive spots of the two recombinant adenovirus vector Ebola vaccines (with and without GP gene codon optimization) immunized mouse were no significantly different, and the result was accordant with that of the intracellular cytokine staining.

5. Conclusion of the Immunological Evaluation

After GP gene codon optimization, although the cellular immune response of the recombinant adenovirus vector Ebola vaccine on the mouse model was not changed, the humoral immune response was greatly increased. Cellular immune response and humoral immune reponse are both significant to prevent Ebola virus infection. Study on animal model in recent years shows that the Ebola GP specific IgG antibody level is relatively higher in correlation with protection efficacy than that of the cellular immune response (Wong, G., Richardson, J. S., Pihhet, S., Patel, A., Qiu, X., Alimonti, J., . . . Kobinger, G. P. (2012). Immune parameters correlate with protection against Ebola virus infection in rodents and nonhuman primates. SciTransl Med, 4(158), 158 ra146.doi:10.1126/scritranslmed.3004582). The subsequent study shows that monoclonal antibody mixture ZMapp has a 100% treatment effect on rhesus with conspicuous symptoms 5 days after Ebola challenge (Qiu, X., Wong, G., Audet, J., . . . Kobinger, G. P. (2014). Reversion of advanced Ebola virus disease in nonhuman primates with ZMapp. Nature, 514 (7520), 47-53.doi:10.1038/nature13777). Although the treatment effect of ZMapp on human has no related clinical demonstration, some patients treated with ZMapp did survive in the Ebola epidemic events in the West Africa, and the result sufficiently shows the significance of the specific Ebola GP antibody in preventing Ebola virus infection. After the GP gene is subjected to codon optimization, not only is the antibody generation time brought ahead of time, but also the antibody titer is greatly increased. Due to the codon optimization, the effect of the vaccine on the Ebola virus infection can be improved to a very large extent.

The present invention discloses an Ebola vaccine with a replication-defective human adenovirus as a vector, a preparation method thereof and a use of the recombinant adenovirus vector in preparing a vaccine. The said vaccine for preventing Ebola virus diseases can be easily industrialized, showing the industrial applicability.

The invention claimed is:

1. A nucleotide sequence encoding the glycoprotein of Ebola virus comprising SEQ ID NO: 1.

2. A vector comprising the nucleotide sequence of claim 1.

3. The vector of claim 2, wherein the vector is pDC316.

4. A replication-defective recombinant human adenovirus capable of expressing the nucleotide sequence of claim 1.

5. The recombinant adenovirus of claim 4, wherein the recombinant adenovirus vector is derived from an AdMax adenovirus system.

6. A use of the recombinant adenovirus vector of claim 5 in preparing a vaccine preventing Ebola virus diseases.

7. The use of claim 6, wherein the recombinant adenovirus is prepared as an injection.

8. A method for preparing the replication-defective recombinant human adenovirus of claim 5, which comprises the following steps:
   (1) Constructing a shuttle plasmid vector comprising the nucleotide coding sequences of Ebola virus glycoprotein;
   (2) Co-transfection of the vector of step (1) and backbone plasmids into a host cell;
   (3) Culturing the host cell of step (2);
   (4) Harvesting the replication-defective recombinant human adenovirus released from the cells of step (3).

9. The method of claim 8, wherein the vector of step (1) is pDC316.

10. The method of claim 8, wherein the backbone plasmids of step (2) are pBHGlox_E1, 3Cre.

11. The method of claim 8, wherein the cell of step (3) is HEK 293 cell.

12. The method of claim 8, wherein the recombinant adenovirus is extracted and purified through a two-step column chromatography method with Source 30Q and Sepharose 4FF in step (4).

* * * * *